(12) United States Patent
Gray et al.

(10) Patent No.: US 6,465,182 B1
(45) Date of Patent: Oct. 15, 2002

(54) COMPARATIVE FLUORESCENCE HYBRIDIZATION TO OLIGONUCLEOTIDE MICROARRAYS

(75) Inventors: Joe Gray, San Francisco; Dan Pinkel, Walnut Creek; Donna Albertson, Lafayette; Colin Collins, San Rafael; Russell Baldocchi, San Francisco, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/302,056

(22) Filed: Apr. 29, 1999

(51) Int. Cl.$^7$ .............................. C12Q 1/68; C12P 19/34; C07H 21/04; C07H 21/02; C07H 19/04
(52) U.S. Cl. ..................... 435/6; 435/91.1; 435/91.2; 536/24.3; 536/24.33; 536/26.6; 536/23.1
(58) Field of Search .................. 435/6, 91.2; 536/24.3, 536/24.33, 26.6

(56) References Cited

U.S. PATENT DOCUMENTS 5,665,549 A 9/1997 Pinkel et al. ................ 435/6
5,830,645 A * 11/1998 Pinkel et al. ................ 435/6

OTHER PUBLICATIONS

Lisitsyn et al. Cloning the difference between two complex genomes. Science. vol. 259, pp. 946–951, Feb. 1993.*
Lamb et al. Gene Probes 1, A practical Approach. Oxford University Press. pp. 4–9, Apr. 1995.*
Barringer, et al., "Blunt–end and single–strand ligations by *Escherichia coli* ligase: influence on an in vitro amplification scheme"; *Gene*, vol. 89 pp. 117–122 (1990).
Hames and Higgins *Gene Probes 1 A Practical Approach*, pp. 1–9, Published by Oxford University Press, (1995).
Kallioniemi, et al., "Comparative Genomic Hybridization for Molecular Cytogenetic Analysis of Solid Tumors"; *Science*, vol. 258, pp. 818–821 (Oct. 1992).
Klein, et al., "Comparative genomic hybridization, loss of heterozygosity, and DNA sequence analysis of single cells"; *Proc. Natl. Acad. USA*, vol. 96, pp. 4494–4499 (Apr. 1999).
Landegren, et al., "A Ligase–Mediated Gene Detection Technique"; *Science*, vol. 241 pp. 1077–1080,, (Aug. 1988).
Lie, et al., "Advances in quantitative PCR technology: 5' nuclease assays" *Current Opinion in Biotechnology* vol. 9:43–48 (1998).
Lisitsyn, et al., "Cloning the Differences Between Two Complex Genomes" *Science*, vol. 259 pp. 946–951 (Feb. 1993).
Orlando, et al., "Developments in Quantitative PCR"; *Clin. Chem. Lab. Med.*, 36(5):255–269 (1998).
Pinkel, et al., "High resolution analysis of DNA copy number variation using comparative genomic hybridization to microarrays"; *Nature Genetics*, vol. 20, pp. 207–211 (Oct. 1998).
Wu, et al. "The Ligation Amplification Reaction (LAR)–Amplification of Specific DNA Sequences Using Sequential Rounds of Template–Dependent Ligation"; *Genomics*, vol. 4 pp. 560–569 (1989).

* cited by examiner

*Primary Examiner*—Kenneth R. Horlick
*Assistant Examiner*—Alexander H. Spiegler
(74) *Attorney, Agent, or Firm*—Townsend and Townsend and Crew, LLP

(57) ABSTRACT

The present invention provides methods of determining relative copy number of target nucleic acid sequences and precise mapping of chromosomal abnormalities associated with disease. The methods of the invention use target nucleic acid sequences immobilized on a solid surface, to which a sample comprising two sets of differentially labeled nucleic acid sequences are hybridized. The hybridization of the labeled nucleic acid sequences to the solid surface is then detected using standard techniques.

12 Claims, 1 Drawing Sheet

COMPARATIVE FLUORESCENCE HYBRIDIZATION TO OLIGONUCLEOTIDE MICROARRAYS

STATEMENT AS TO RIGHTS TO INVENTIONS MADE UNDER FEDERALLY SPONSORED RESEARCH AND DEVELOPMENT

This invention was made with Government support under Grant No. C58207, awarded by the National Institutes of Health. The Government has certain rights in this invention.

BACKGROUND OF THE INVENTION

The present invention relates to improved methods for detecting and mapping genetic abnormalities associated with various diseases. In particular, it relates to the use of nucleic acid hybridization methods for comparing copy numbers of particular nucleic acid sequences in a collection of sequences relative to the copy number of these sequences in other collections of sequences.

Many genomic and genetic studies are directed to the identification of differences in gene dosage or expression among cell populations for the study and detection of disease. For example, many malignancies involve the gain or loss of DNA sequences resulting in activation of oncogenes or inactivation of tumor suppressor genes. Identification of the genetic events leading to neoplastic transformation and subsequent progression can facilitate efforts to define the biological basis for disease, improve prognostication of therapeutic response, and permit earlier tumor detection. In addition, perinatal genetic problems frequently result from loss or gain of chromosome segments such as trisomy 21 or the micro deletion syndromes.

Cytogenetics is the traditional method for detecting amplified or deleted chromosomal regions. More recent methods permit assessing the amount of a given nucleic acid sequence in a sample using molecular techniques. These methods (e.g., Southern blotting) employ cloned DNA or RNA probes that are hybridized to isolated DNA. Southern blotting and related techniques are effective even if the genome is heavily rearranged so as to eliminate useful karyotype information. However, these methods require use of a probe specific for the sequence to be analyzed. Thus, it is necessary to employ very many individual probes, one at a time, to survey the entire genome of each specimen, if no prior information on particular suspect regions of the genome is available.

Comparative genomic hybridization (CGH) is a recent approach to detect the presence and identify the location of amplified or deleted sequences. See, Kallioniemi et al., Science 258: 818–821 (1992) and U.S. Pat. No. 5,665,549). CGH reveals increases and decreases irrespective of genome rearrangement. In one implementation of CGH, genomic DNA is isolated from normal reference cells, as well as from test cells (e.g., tumor cells). The two nucleic acid sequences are differentially labeled and then hybridized in situ to metaphase chromosomes of a reference cell. The repetitive sequences in both the reference and test DNAs are either removed or their hybridization capacity is reduced by some means. Chromosomal regions in the test cells which are at increased or decreased copy number can be quickly identified by detecting regions where the ratio of signal from the two DNAs is altered. For example, those regions that have been decreased in copy number in the test cells will show relatively lower signal from the test DNA than the reference compared to other regions of the genome. Regions that have been increased in copy number in the test cells will show relatively higher signal from the test DNA.

Improved CGH techniques have also been described. For instance, CGH applied to arrays allows for more precise localization of chromosome abnormalities than use of a metaphase spreads as the target (see U.S. Pat. No. 5,830,645).

Despite these improvements, there is a constant need for improved methods of genetic analysis that provide fast, reliable results. The present invention addresses these and other needs.

SUMMARY OF THE INVENTION

The present invention provides methods for quantitatively comparing the copy number of a nucleic acid sequence in a first collection of labeled nucleic acid molecules relative to the copy number of that same sequence in a second collection of labeled nucleic acid sequences. The method comprises labeling the nucleic acid molecules in the first collection and the nucleic acid molecules in the second collection with first and second labels, respectively. The first and second labels should be distinguishable from each other. The collections are contacted to a plurality of target oligonucleotides (a microarray) under conditions such that nucleic acid hybridization to the target elements can occur. The two collections can be contacted to the target elements either simultaneously or serially.

The two collections of labeled nucleic acid sequences are prepared by specifically amplifying sequences that hybridize specifically to the target oligonucleotides from source. This amplification produces a representative collection of nucleic acid sequences, meaning that the amplification is both quantitative and results in a collection of reduced complexity. As explained below, a representative collection of nucleic acid sequences is one in which the relative abundance of particular sequences in the source nucleic acids is maintained in the labeled nucleic acids used in the assays of the invention (i.e. is quantitative). In addition, the collection of labeled nucleic acid sequences has much lower complexity as compared to the source nucleic acid molecules. The reduced complexity is advantageous because the rate of hybridization is enhanced, as compared to hybridization using highly complex collections of labeled nucleic acid sequences.

The target oligonucleotides and the labeled nucleic acid sequences may be, for example, RNA, DNA, or cDNA. The nucleic acid sequences may be derived from any organism. Usually the nucleic acid in the target elements and the labeled nucleic acid sequences are from the same species.

The target elements are typically arranged in separate discrete locations on a solid surface. The target oligonucleotides in a target element are those for which comparative copy number information is desired. For example, the oligonucleotides may originate from a chromosomal location known to be associated with disease, may be selected to be representative of a chromosomal region whose association with disease is to be tested, or may correspond to genes whose transcription is to be assayed.

After contacting the labeled nucleic acid sequences to the target elements the amount of binding of each, and the binding ratio is determined for each target element. Typically the greater the ratio of the binding to a target element the greater the copy number ratio of sequences in the two labeled nucleic acid sequences that bind to that element. Thus comparison of the ratios among target elements permits comparison of copy number ratios of different sequences in the labeled nucleic acid sequences.

The methods are typically carried out using techniques suitable for fluorescence in situ hybridization. Thus, the first and second labels are usually fluorescent labels.

In a typical embodiment, one collection of labeled nucleic acid sequences is prepared from a test cell, cell population, or tissue under study; and the second collection of labeled nucleic acid sequences is prepared from a reference cell, cell population, or tissue. Reference cells can be normal non-diseased cells, or they can be from a sample of diseased tissue that serves as a standard for other aspects of the disease. For example, if the reference nucleic acid is genomic DNA isolated from normal cells, then the copy number of each sequence in that collection relative to the others is known (e.g., two copies of each autosomal sequence, and one or two copies of each sex chromosomal sequence depending on gender). Comparison of this to DNA prepared from a test cell permits detection in variations from normal.

Alternatively the reference collection of labeled nucleic acid sequences may be prepared from genomic DNA from a primary tumor which may contain substantial variations in copy number among its different sequences, and the test may be prepared from genomic DNA of metastatic cells from that tumor, so that the comparison shows the differences between the primary tumor and its metastasis. Further, both collections may be prepared from normal cells. For example comparison of mRNA populations between normal cells of different tissues permits detection of differential gene expression that is a critical feature of tissue differentiation. Thus in general the terms test and reference are used for convenience to distinguish the two collections, but they do not imply other characteristics of the nucleic acid sequences they contain.

The invention also provides kits comprising materials useful for carrying out the methods of the invention. Kits of the invention comprise a solid support having an array of target nucleic acid sequences bound thereto and a container containing nucleic acid sequencess representing a normal reference genome, or cDNA from a reference cell type, and the like. The kit may further comprise two different fluorochromes, reagents for labeling the test genomes, alternate reference genomes and the like.

Definitions The term "complexity" is used here according to standard meaning of this term as established by Britten et al., *Methods of Enzymol.* 29:363 (1974). See, also Cantor and Schimmel *Biophysical Chemistry*: Part III at 1228–1230 for further explanation of nucleic acid complexity.

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences. A "stringent hybridization" and "stringent hybridization wash conditions" in the context of nucleic acid hybridization (e.g., as in array, Southern or Northern hybridizations) are sequence dependent, and are different under different environmental parameters. An extensive guide to the hybridization of nucleic acids is found in, e.g., Tijssen (1993) *Laboratory Techniques in Biochemistry and Molecular Biology— Hybridization with Nucleic Acid Probes part I, chapt 2, "Overview of principles of hybridization and the strategy of nucleic acid probe assays,"* Elsevier, N.Y. ("Tijssen"). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook (1989) *Molecular Cloning: A Laboratory Manual* (2nd ed.) VoL 1–3, Cold Spring Harbor Laboratory, Cold Spring Harbor Press, N.Y., and detailed discussion, below), with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, e.g., Sambrook supra.) for a description of SSC buffer). A typical stringent wash for an array hybridization is 50% formamide, 2×SSC at 35° C. to 60° C. Often, a high stringency wash is preceded by a low stringency wash to remove background probe signal. An example medium stringency wash for a duplex of, e.g., more than 100 nucleotides, is 1×SSC at 45° C. for 15 minutes. An example of a low stringency wash for a duplex of, e.g., more than 100 nucleotides, is 4×to 6×SSC at 40° C. for 15 minutes.

The term "labeled nucleic acid sequence", as used herein, refers to a nucleic acid molecule attached to a detectable composition, i.e., a label. The detection can be by, e.g., spectroscopic, photochemical, biochemical, immunochemical, physical or chemical means. For example, useful labels include $^{32}P$, $^{3}S$, $^{3}H$, $^{14}C$, $^{125}I$, $^{131}I$; fluorescent dyes (e.g., FITC, rhodamine, lanthanide phosphors, Texas red), electron-dense reagents (e.g. gold), enzymes, e.g., as commonly used in an ELISA (e.g., horseradish peroxidase, beta-galactosidase, luciferase, alkaline phosphatase), colorimetric labels (e.g. colloidal gold), magnetic labels (e.g. Dynabeads™), biotin, dioxigenin, or haptens and proteins for which antisera or monoclonal antibodies are available. The label can be directly incorporated into the nucleic acid, peptide or other target compound to be detected, or it can be attached to a probe or antibody that hybridizes or binds to the target. A peptide can be made detectable by incorporating predetermined polypeptide epitopes recognized by a secondary reporter (e.g., leucine zipper pair sequences, binding sites for secondary antibodies, transcriptional activator polypeptide, metal binding domains, epitope tags). Label can be attached by spacer arms of various lengths to reduce potential steric hindrance or impact on other useful or desired properties (see, e.g., Mansfield (1995) *Mol Cell Probes* 9: 145–156). It will be appreciated that combinations of labels can also be used. Thus, for example, in some embodiments, different nucleic acid sequences may be labeled with distinguishable (e.g. differently colored) labels.

The term "nucleic acid" as used herein refers to a deoxyribonucleotide or ribonucleotide in either single- or double-stranded form. The term encompasses nucleic acids, i.e., oligonucleotides, containing known analogues of natural nucleotides which have similar or improved binding properties, for the purposes desired, as the reference nucleic acid. The term also includes nucleic acids which are metabolized in a manner similar to naturally occurring nucleotides or at rates that are improved thereover for the purposes desired. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs);

see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923–1937; Antisense Research and Applications (1993, CRC Press). PNAs contain non-ionic backbones, such as N-(2-aminoethyl) glycine units. Phosphorothioate linkages are described in WO 97/03211; WO 96/39154; Mata (1997) *Toxicol. Appl. Pharmacol.* 144:189–197. Other synthetic backbones encompassed by the term include methylphosphonate linkages or alternating methylphosphonate and phosphodiester linkages (Strauss-Soukup (1997) *Biochemistry* 36: 8692–8698), and benzylphosphonate linkages (Samstag (1996) *Antisense Nucleic Acid Drug Dev* 6: 153–156). The term nucleic acid is used interchangeably with gene, cDNA, mRNA, oligonucleotide primer, probe and amplification product.

A "nucleic acid microarray" or "nucleic acid array" is a plurality of target elements, each comprising a target oligonucleotide immobilized on a solid surface to which labeled nucleic acids are hybridized. "Target oligonucleotides" of a target element are usually between about 10 to about 500 nucleotides, more usually between about 25 to about 250 nucleotides, and typically between about 50 and about 100 nucleotides in length. The oligonucleotides usually have their origin in a defined region of the genome. The target nucleic acids of a target element may, for example, contain sequences from specific genes or, be from a chromosomal region suspected of being present at increased or decreased copy number in cells of interest, e.g., tumor cells. The target element may also be prepared from MRNA, or cDNA derived from such MRNA, suspected of being transcribed at abnormal levels.

Alternatively, a target element may comprise nucleic acid sequences of unknown significance or location. An array of such elements could represent locations that sample, either continuously or at discrete points, any desired portion of a genome, including, but not limited to, an entire genome, a single chromosome, or a portion of a chromosome. The number of target elements and the complexity of the nucleic acids in each would determine the density of sampling. Similarly, an array of targets elements comprising nucleic acids from anonymous cDNA clones (including those containing 5' untranslated regions or promoter sequences) permits identification of those that might be differentially expressed in some cells of interest, thereby focusing attention on study of these genes.

Generally, smaller target elements are preferred. Typically, a target element will be about 1 mm or less in diameter. Generally element sizes can be from 1μm to about 3 mm, preferably they are between about 5μm and about 1 mm. The target elements of the arrays may be arranged on the solid surface at different densities. The target element densities will depend upon a number of factors, such as the nature of the label, the solid support, and the like. Techniques capable of producing high density arrays can also be used for this purpose (see, e.g., Fodor (1991) *Science* 767–773; Johnston (1998) *Curr. Biol.* 8: R171–R174; Schummer (1997) *Biotechniques* 23: 1087–1092; Kern (1997) *Biotechniques* 23: 120–124; U.S. Pat. No. 5,143, 854).

The term "relative copy number" refers to the number of copies of one nucleic acid molecule or sequence relative to that of another molecule or sequence within a single collection of nucleic acid molecules. The term can also refer to a comparison of the number of copies of the same sequence present in two collections of nucleic acid molecules.

A "representative collection of nucleic acid sequences of reduced complexity" is a collection of nucleic acid sequences prepared using amplification techniques (e.g. PCR) and labeled as described below. The amplification methods are quantitative so that the relative copy number of particular sequences within a source nucleic acid is maintained in the amplified, labeled nucleic acid sequences used in the assays. In the context of this invention such a collection of labeled nucleic acid sequences is said to be representative of the source from which it is derived. In addition, as a result of the specific amplification of particular sequences, the complexity of the labeled nucleic acid sequences is much less than that of the source. The reduced complexity is advantageous because the hybridization time is shortened as compared to hybridization with more complex mixtures of labeled nucleic acid sequences.

A "source of nucleic acid" or "source nucleic acid" as used herein is a sample comprising DNA or RNA (typically human) in a form suitable for amplification in the methods of the invention. The nucleic acid may be isolated, cloned or amplified; it may be, e.g., genomic DNA, mRNA, or cDNA from a particular chromosome, or selected sequences (e.g. particular promoters, genes, amplification or restriction fragments, cDNA, etc.) within particular amplicons or deletions known in the art. The nucleic acid sample may be extracted from particular cells or tissues. For example, the cell or tissue sample from which the nucleic acid sample is prepared may be taken from a patient suspected of having cancer associated with the amplicon amplification or deletion or translocation being detected. Methods of isolating cell and tissue samples are well known to those of skill in the art and include, but are not limited to, aspirations, tissue sections, needle biopsies, and the like. Frequently the sample will be a "clinical sample" which is a sample derived from a patient, including sections of tissues such as frozen sections or paraffin sections taken for histological purposes. The sample can also be derived from supernatants (of cells) or the cells themselves from cell cultures, cells from tissue culture and other media in which it may be desirable to detect chromosomal abnormalities or determine amplicon copy number.

DESCRIPTION OF THE PREFERRED EMBODIMENTS

Figure 1:
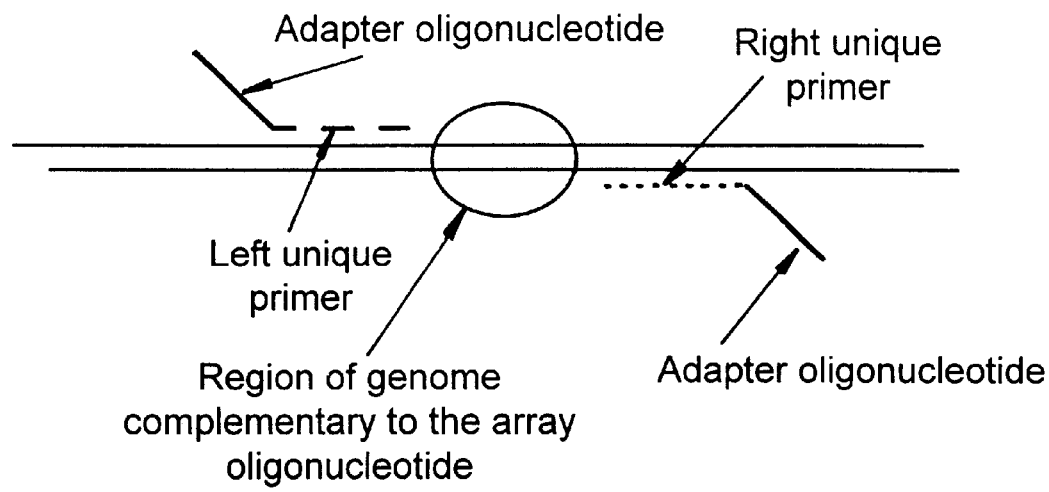
FIG. 1 is a schematic drawing of the PCR amplification methods of the invention.

The present invention provides methods for comparing abnormal nucleic acid copy number and mapping of chromosomal abnormalities associated with disease. The methods of the invention use target oligonucleotides immobilized on a solid support to which differentially labeled nucleic acid sequences are hybridized. The labeled nucleic acid sequences are prepared by specifically amplifying sequences that specifically hybridize (i.e., are substantially identical) to the target oligonucleotide sequences. Typically, this is done using PCR primers that flank the target sequences in a collection of source nucleic acid sequences (e.g., genomic DNA isolated from cells of interest). The hybridization of the labeled nucleic acids to the target is then detected using standard techniques. For a description of array-based hybridization systems, see Pinkel et al. (1998) *Nature Genetics*, 20: 207–211 and U.S. Pat. No. 5,830,645.

In the preferred embodiments, neither the target elements nor the labeled nucleic acid sequences comprise repetitive DNA sequences. As a result, the methods of the present invention do not require techniques designed to inhibit hybridization of repetitive sequences (e.g., use of unlabeled blocking nucleic acids enriched for repetitive sequences). The methods thus provide quicker results than methods in which repetitive sequences are present in the target nucleic acid sequences and/or labeled nucleic acid sequences.

The methods of the invention compare the copy numbers of sequences capable of binding to the target elements. Variations in copy number detectable by the methods of the invention may arise in different ways. For example, copy number may be altered as a result of amplification or deletion of a chromosomal region. Alternatively, copy number may be reduced by genetic rearrangements that alter the sequences in the labeled nucleic acid sequences or target nucleic acid sequences sufficiently to reduce their binding.

Target Nucleic Acid Sequences

Target nucleic acid sequences of the invention can be derived from virtually any source. Typically, the targets will be nucleic acid molecules derived from representative locations along a chromosome of interest, a chromosomal region of interest, an entire genome of interest, a cDNA library, and the like. These target oligonucleotides may be derived, for instance, from genomic clones, restriction digests of genomic clone, cDNA clones and the like. In some embodiments the target nucleic acid sequences are derived from a previously mapped library of clones spanning a particular region of interest.

The choice of target nucleic acids to use may be influenced by prior knowledge of the association of a particular chromosome or chromosomal region with certain disease conditions. For example, WO98/02539, discloses an amplicon on chromosome 20 that is associated with cancer. Alternatively, whole genome screening to identify a new region subject to frequent changes in copy number can be performed using the methods of the present invention. In these embodiments, target elements usually contain nucleic acid sequences representative of locations distributed over the entire genome. In some embodiments (e.g., using a large number of target elements of high complexity) all sequences in the genome can be present in the array.

The oligonucleotides used on the microarrays are typically prepared using previously genetically or physically mapped sequences. For example, sequence tagged sites (STS) which are used to "tag," or identify particular DNA segments in the genome can be used. To assign an STS designation, each cloned DNA segment is sequenced over an approximately 200 to 500 base pair region. With this sequence data, PCR primers are designed and tested to ensure they can be used to identify, "tag", or synthesize that particular sequence by PCR amplification. Submission of segment and primer sequences, and PCR assay conditions to public databases allows anyone to rapidly and conveniently identify virtually any genomic clone or fragment. See, e.g., Olson, *Science* 245:1434–1435 (1989). Alternatively, expressed sequence tags (EST) can be used to prepare the arrays of the invention.

In preferred embodiments, the target oligonucleotide sequences lack repetitive sequences and are relatively uniform in base composition and length. In the absence of repetitive sequences in either the target or labeled nucleic acid sequences, there is no need for means to inhibit hybridization of these sequences. Since base composition and length can effect hybridization, maintaining uniformity of these two factors ensures more consistent results among elements within an array.

Preparation of Microarrays of the Invention

Microarrays of the invention comprise a multiplicity of different "probe" or "target" nucleic acids (or other compounds) attached to one or more surfaces (e.g., solid, membrane, or gel). In a preferred embodiment, the multiplicity of nucleic acids (or other moieties) is attached to a single contiguous surface or to a multiplicity of surfaces juxtaposed to each other.

In an array format a large number of different hybridization reactions can be run essentially "in parallel." This provides rapid, essentially simultaneous, evaluation of a number of hybridizations in a single "experiment". Methods of performing hybridization reactions in array based formats are well known to those of skill in the art (see, e.g., Pastinen (1997) Genome Res. 7: 606–614; Jackson (1996) *Nature Biotechnology* 14:1685; Chee (1995) *Science* 274: 610; WO 96/17958, Pinkel et al. (1998) *Nature Genetics* 20: 207–211).

Arrays, particularly nucleic acid arrays can be produced according to a wide variety of methods well known to those of skill in the art. For example, in a simple embodiment, "low density" arrays can simply be produced by spotting (e.g. by hand using a pipette) different nucleic acids at different locations on a solid support (e.g. a glass surface, a membrane, etc.).

This simple spotting, approach has been automated to produce high density spotted arrays (see, e.g., U.S. Pat. No: 5,807,522). This patent describes the use of an automated system that taps a microcapillary against a surface to deposit a small volume of a biological sample. The process is repeated to generate high density arrays.

Microarrays of the invention can also be produced using oligonucleotide synthesis technology. Thus, for example, Fodor et al. *Science* 767–773 (1991), U.S. Pat. No. 5,143,854 and PCT Patent Publication Nos. WO 90/15070 and 92/10092 teach the use of light-directed combinatorial synthesis of high density oligonucleotide arrays.

Many methods for immobilizing nucleic acids on a variety of solid surfaces are known in the art. A wide variety of organic and inorganic polymers, as well as other materials, both natural and synthetic, can be employed as the material for the solid surface. Illustrative solid surfaces include, e.g., nitrocellulose, nylon, glass, quartz, diazotized membranes (paper or nylon), silicones, polyformaldehyde, cellulose, and cellulose acetate. In addition, plastics such as polyethylene, polypropylene, polystyrene, and the like can be used. Other materials which may be employed include paper, ceramics, metals, metalloids, semiconductive materials, cermets or the like. In addition, substances that form gels can be used. Such materials include, e.g., proteins (e.g., gelatins), lipopolysaccharides, silicates, agarose and polyacrylamides. Where the solid surface is porous, various pore sizes may be employed depending upon the nature of the system.

In preparing the surface, a plurality of different materials may be employed, particularly as laminates, to obtain various properties. For example, proteins (e.g., bovine serum albumin) or mixtures of macromolecules (e.g., Denhardt's solution) can be employed to avoid non-specific binding, simplify covalent conjugation, enhance signal detection or the like. If covalent bonding between a compound and the surface is desired, the surface will usually be polyfinctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature.

For example, methods for immobilizing nucleic acids by introduction of various functional groups to the molecules is known (see, e.g., Bischoff (1987) *Anal. Biochem.,* 164: 336–344; Kremsky (1987) *Nucl. Acids Res.* 15: 2891–2910). Modified nucleotides can be placed on the target using PCR primers containing the modified nucleotide, or by enzymatic end labeling with modified nucleotides. Use of glass or membrane supports (e.g., nitrocellulose, nylon, polypropylene) for the nucleic acid arrays of the invention is advantageous because of well developed technology employing manual and robotic methods of arraying targets at relatively high element densities. Such membranes are generally available and protocols and equipment for hybridization to membranes is well known.

Target elements of various sizes, ranging from 1 mm diameter down to 1 $\mu$m can be used. Smaller target elements containing low amounts of concentrated, fixed DNA are used for high complexity comparative hybridizations since the total amount of sample available for binding to each target element will be limited. Thus it is advantageous to have small array target elements that contain a small amount of concentrated target DNA so that the signal that is obtained is highly localized and bright. Such small array target elements are typically used in arrays with densities greater than $10^4/cm^2$. Relatively simple approaches capable of quantitative fluorescent imaging of 1 $cm^2$ areas have been described that permit acquisition of data from a large number of target elements in a single image (see, e.g., Wittrup (1994) *Cytometry* 16:206–213, Pinkel et al. (1998) *Nature Genetics* 20: 207–211).

Arrays on solid surface substrates with much lower fluorescence than membranes, such as glass, quartz, or small beads, can achieve much better sensitivity. Substrates such as glass or fused silica are advantageous in that they provide a very low fluorescence substrate, and a highly efficient hybridization environment. Covalent attachment of the target nucleic acids to glass or synthetic fused silica can be accomplished according to a number of known techniques (described above). Nucleic acids can be conveniently coupled to glass using commercially available reagents. For instance, materials for preparation of silanized glass with a number of functional groups are commercially available or can be prepared using standard techniques (see, e.g., Gait (1984) Oligonucleotide Synthesis: A Practical Approach, IRL Press, Wash., D.C.). Quartz cover slips, which have at least 10-fold lower autofluorescence than glass, can also be silanized.

Alternatively, targets can also be immobilized on commercially available coated beads or other surfaces. For instance, biotin end-labeled nucleic acids can be bound to commercially available avidin-coated beads. Streptavidin or anti-digoxigenin antibody can also be attached to silanized glass slides by protein-mediated coupling. A following standard protocols (see, e.g., Smith (1992) *Science* 258: 1122–1126). Biotin or digoxigenin end-labeled nucleic acids can be prepared according to standard techniques. Hybridization to nucleic acids attached to beads is accomplished by suspending them in the hybridization mix, and then depositing them on the glass substrate for analysis after washing. Alternatively, paramagnetic particles, such as ferric oxide particles, with or without avidin coating, can be used.

In one particularly preferred embodiment, target nucleic acid is spotted onto a surface (e.g., a glass or quartz surface). The nucleic acid is dissolved in a mixture of water, dimethylsulfoxide (DMSO), and nitrocellulose and spotted onto amino-silane coated glass slides. Small capillaries tubes can be used to "spot" the target mixture.

Preparation of labeled nucleic acid sequences

As with target nucleic acid sequences, a wide variety of nucleic acids can be used as the source of the labeled nucleic acid sequences in the methods of the present invention. The labeled nucleic acid sequences may be prepared from, for example, genomic DNA representing the entire genome from a particular organism, tissue or cell type or may comprise a portion of the genome, such as a single chromosome.

To compare expression levels of a particular gene or genes, the labeled nucleic acid sequences can be derived from MRNA or cDNA prepared from an organism, tissue, or cell of interest. For instance, test cDNA or mRNA, along with MRNA or cDNA from normal reference cells, can be used to prepare labeled nucleic acid sequences which are hybridized to an array of oligonucleotides from a normalized cDNA library. In addition, labeled nucleic acid sequences made from genomic DNA from two cell populations can be hybridized to oligonucleotide microarray prepared from cDNA to detect those cDNAs that come from regions of variant DNA copy number in the genome.

The methods of the invention are suitable for comparing copy number of particular sequences in any combination of two or more populations of nucleic acid sequences. One of skill will recognize that the particular populations of sample nucleic acid sequences being compared is not critical to the invention. For instance, genomic or cDNA can be compared from two related species. Alternatively, levels of expression of particular genes in two or more tissue or cell types can be compared. As noted above, the methods are particularly useful in the diagnosis of disease.

Standard procedures can be used to isolate nucleic acids used as the source of the labeled nucleic acid sequences of the invention (either DNA or mRNA) from appropriate tissues (see, e.g., Sambrook, et al., Molecular Cloning - A Laboratory Manual, Cold Spring Harbor Laboratory, Cold Spring Harbor, N.Y. (1985)). Conventional methods for preparation of cDNA from MRNA can also be used.

The particular cells or tissue from which the source nucleic acids are isolated will depend upon the particular application. Typically, for detection of abnormalities associated with cancer, genomic DNA is isolated from tumor cells. For prenatal detection of disease, fetal tissue will be used.

As noted above, the labeled nucleic acid sequences of the invention are prepared by specifically amplifying sequences from the source nucleic acids. Means for specific amplification of desired sequences are well known to those of skill. Typically, the polymerase chain reaction (PCR) is used. Thus, primers are selected that hybridize to regions that flank the target sequences on the microarray. Since the relative amounts of sequences that specifically hybidize to the targets is analyzed in the methods of the invention, the amount of amplification product should be proportional to the amount of template in the original sample. Methods of "quantitative" amplification are well known to those of skill in the art. For example, quantitative PCR can involve simultaneously coamplifying a known quantity of a control sequence using the same primers. This provides an internal standard that may be used to calibrate the PCR reaction. Alternatively, kits for quantitive PCR methods are commercially available (e.g. TaqMan® Assay Reagents, available from Perkin Elmer/Applied Biosystems). Quantitative PCR methods are described in Lie and Petropoulos. *Curr Opin Biotechnol* 9: 43–48 (1998); Orlando, et al *Clin Chem Lab Med* 36: 255–269 (1998) and Innis et aL (1990) PCR *Protocols, A Guide to Methods and Applications*, Academic Press, Inc. N.Y.).

In preferred methods, the PCR primers contain an adapter sequence that is substantially absent from the source nucleic acids (FIG. 1). The preferred length of the primers is usually between about 40 and about 70 nucleotides and typically between about 50 and about 60 nucleotides. After a limited number of cycles of amplification using these primers (usually 2 to about 5 cycles), amplification is then continued using primers that specifically hybridize to the adapter sequences. This techniques helps to ensure that only the target sequences in the source nucleic acids are amplified further. In addition, it ensures that amplification is uniform among all the sequences in the source nucleic acid.

Other suitable amplification methods include, but are not limited to ligase chain reaction (LCR) (see Wu and Wallace (1989) *Genomics* 4: 560, Landegren et al. (1988) *Science* 241: 1077, and Barringer et al. (1990) *Gene* 89: 117, transcription amplification (Kwoh et al. (1989) *Proc. Natl. Acad. Sci. USA* 86: 1173), self-sustained sequence replication (Guatelli et al. (1990) *Proc. Nat. Acad. Sci. USA* 87: 1874), dop PCR, and linker adapter PCR (Klein et al. (1999) *Proc. Natl. Acad. Sci. U.S.A.* 96:4494), etc.

Labelling nucleic acids

The labels used in the invention may be incorporated into the nucleic acids by any of a number of means well known to those of skill in the art. Means of attaching labels to nucleic acids include, for example nick translation, or end-labeling by kinasing of the nucleic acid and subsequent attachment (ligation) of a linker joining the sample nucleic acid to a label (e.g., a fluorophore). A wide variety of linkers for the attachment of labels to nucleic acids are also known. In addition, intercalating dyes and fluorescent nucleotides can also be used. In a preferred embodiment, fluorescent nucleotides are incorporated into the amplified sequences using either the Klenow fragment of DNA Polymerase I or Taq DNA polymerase and primers for the adapter sequences.

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like, see, e.g., Molecular Probes, Eugene, Oreg., USA), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold (e.g., gold particles in the 40–80 mn diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

A fluorescent label is preferred because it provides a very strong signal with low background. It is also optically detectable at high resolution and sensitivity through a quick scanning procedure. The nucleic acid samples can all be labeled with a single label, e.g., a single fluorescent label. Alternatively, in another embodiment, different nucleic acid samples can be simultaneously hybridized where each nucleic acid sample has a different label. For instance, one target could have a green fluorescent label and a second target could have a red fluorescent label. The scanning step will distinguish sites of binding of the red label from those binding the green fluorescent label. Each nucleic acid sample (target nucleic acid) can be analyzed independently from one another.

Suitable chromogens which can be employed include those molecules and compounds which absorb light in a distinctive range of wavelengths so that a color can be observed or, alternatively, which emit light when irradiated with radiation of a particular wave length or wave length range, e.g., fluorescers.

Desirably, fluorescers should absorb light above about 300 nm, preferably about 350 nm, and more preferably above about 400 nm, usually emitting at wavelengths greater than about 10 nm higher than the wavelength of the light absorbed. It should be noted that the absorption and emission characteristics of the bound dye can differ from the unbound dye. Therefore, when referring to the various wavelength ranges and characteristics of the dyes, it is intended to indicate the dyes as employed and not the dye which is unconjugated and characterized in an arbitrary solvent.

Fluorescers are generally preferred because by irradiating a fluorescer with light, one can obtain a plurality of emissions. Thus, a single label can provide for a plurality of measurable events.

Detectable signal can also be provided by chemiluminescent and bioluminescent sources. Chemiluminescent sources include a compound which becomes electronically excited by a chemical reaction and can then emit light which serves as the detectable signal or donates energy to a fluorescent acceptor. Alternatively, luciferins can be used in conjunction with luciferase or lucigenins to provide bioluminescence.

Spin labels are provided by reporter molecules with an unpaired electron spin which can be detected by electron spin resonance (ESR) spectroscopy. Exemplary spin labels include organic free radicals, transitional metal complexes, particularly vanadium, copper, iron, and manganese, and the like. Exemplary spin labels include nitroxide free radicals.

The label may be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see *Laboratory Techniques in Biochemistry and Molecular Biology, Vol. 24: Hybridization With Nucleic Acid Probes*, P. Tijssen, ed. Elsevier, N.Y., (1993)).

Fluorescent labels are easily added during an in vitro transcription reaction. Thus, for example, fluorescein labeled UTP and CTP can be incorporated into the RNA produced in an in vitro transcription.

The labels can be attached directly or through a linker moiety. In general, the site of label or linker-label attachment is not limited to any specific position. For example, a label may be attached to a nucleoside, nucleotide, or analogue thereof at any position that does not interfere with detection or hybridization as desired. For example, certain Label-ON Reagents from Clontech (Palo Alto, Calif.) provide for labeling interspersed throughout the phosphate backbone of an oligonucleotide and for terminal labeling at the 3'and 5'ends. As shown for example herein, labels can be attached at positions on the ribose ring or the ribose can be modified and even eliminated as desired. The base moieties of useful labeling reagents can include those that are naturally occurring or modified in a manner that does not interfere with the purpose to which they are put. Modified bases include but are not limited to 7-deaza A and G, 7-deaza-8-aza A and G, and other heterocyclic moieties.

It will be recognized that fluorescent labels are not to be limited to single species organic molecules, but include inorganic molecules, multi-molecular mixtures of organic and/or inorganic molecules, crystals, heteropolymers, and the like. Thus, for example, CdSe-CdS core-shell nanocrystals enclosed in a silica shell can be easily derivatized for coupling to a biological molecule (Bruchez et al. (1998) *Science*, 281: 2013–2016). Similarly, highly fluorescent quantum dots (zinc sulfide-capped cadmium selenide) have been covalently coupled to biomolecules for use in ultrasensitive biological detection (Warren and Nie (1998) *Science*, 281: 2016–2018).

Hybridization of Labeled Nucleic Acid Sequences to Targets

The copy number of particular nucleic acid sequences in two collections of labeled nucleic acid sequences are compared by hybridizing the nucleic acid sequences to oligonucleotide microarray of the invention. The hybridization signal intensity, and the ratio of intensities, produced by the collections on each of the target elements is determined. Typically the greater the ratio of the signal intensities on a target element the greater the copy number ratio of sequences in the two labeled nucleic acid sequences that bind to that element. Thus comparison of the signal intensity ratios among target elements permits comparison of copy number ratios of different sequences in the labeled nucleic acid sequences.

Standard hybridization techniques are used in the methods of the invention. Suitable methods are described in references describing CGH techniques (Kallioniemi et al., *Science* 258: 818–821 (1992) and WO 93/18186). Several guides to general techniques are available, e.g., Tijssen, *Hybridization with Nucleic Acid Probes*, Parts I and II (Elsevier, Amsterdam 1993). For a descriptions of techniques suitable for in situ hybridizations see, Gall et al. *Meth. Enzymol.*, 21:470–480 (1981) and Angerer et al. in *Genetic Engineering: Principles and Methods* Setlow and Hollaender, Eds. Vol 7, pgs 43–65 (plenum Press, New York 1985).

Generally, nucleic acid hybridizations comprise the following major steps: (1) immobilization of target nucleic acid sequences; (2) prehybridization treatment to increase accessibility of target DNA, and to reduce nonspecific binding; (3) hybridization of the mixture of nucleic acid sequences to the nucleic acid on the solid surface; (4) posthybridization washes to remove nucleic acid fragments not bound in the hybridization and (5) detection of the hybridized nucleic acid fragments. The reagent used in each of these steps and their conditions for use vary depending on the particular application.

Analysis of Detectable Signals From Hybridizations

Standard methods for detection and analysis of signals generated by the labeled nucleic acids can be used. The particular methods will depend upon the labels used in the labeled nucleic acids. Generally, fluorescent labels are preferred. Thus, methods suitable in fluorescence in situ hybridization (FISH) are suitable in the present invention. For instance, the nucleic acid arrays can be imaged in a fluorescence microscope with a polychromatic beam-splitter to avoid color-dependent image shifts. The different color images are acquired with a CCD camera and the digitized images are stored in a computer. A computer program is then used to analyze the signals produced by the array. Methods of visualizing signals are described, for instance, in Kallioniemi et al., supra and in WO 93/18186.

To facilitate the display of results and to improve the sensitivity of detecting small differences in fluorescence intensity, a digital image analysis system is preferably used. A preferred system is QUIPS (an acronym for quantitative image processing system), which is an automated image analysis system based on a standard fluorescence microscope equipped with an automated stage, focus control and filterwheel (Ludl Electronic Products, Ltd., Hawthorne, N.Y.). The filterwheel is mounted in the fluorescence excitation path of the microscope for selection of the excitation wavelength. Special filters (Chroma Technology, Brattleboro, VT.) in the dichroic block allow excitation of the multiple dyes without image registration shift. The microscope has two camera ports, one of which has an intensified CCD camera (Quantex Corp., Sunnyvale, Calif.) for sensitive high-speed video image display which is used for finding interesting areas on a slide as well as for focusing. The other camera port has a cooled CCD camera (model 200 by Photometrics Ltd., Tucson, Ariz.) which is used for the actual image acquisition at high resolution and sensitivity.

The cooled CCD camera is interfaced to a SUN 4/330 workstation (SUN Microsystems, Inc., Mountain View, Calif.) through a VME bus. The entire acquisition of multicolor images is controlled using an image processing software package SCIL-Image (Delft Centre for Image Processing, Delft, Netherlands).

The above is provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A method for comparing copy number of nucleic acid sequences in two or more collections of nucleic acid molecules, the method comprising the steps of:

(a) preparing a first representative collection and a second representative collection of labeled nucleic acid sequences from a first source of nucleic acids and a second source of nucleic acids, respectively, by:

(i) contacting the first source and the second source with primers comprising sequences present in the source nucleic acids and adaptors comprising sequences not present in the source nucleic acids, thereby producing a set of amplified nucleic acids comprising target sequences and (ii) contacting the set of amplified nucleic acids with primers that specifically hybridize to the adaptors, thereby producing first and second collections of labeled nucleic acid sequences of reduced complexity as compared to the first source of nucleic acids and second source of nucleic acids;

wherein the first and second labeled collections are distinguishable from each other;

(b) contacting the first and second collections with a plurality of target elements comprising target oligonucleotides bound to a solid surface;

wherein the first collection of labeled nucleic acid sequences comprises a sequence that specifically hybridizes to a target oligonucleotide;

wherein the second collection of labeled nucleic acid sequences comprises a sequence that specifically hybridizes to the target oligonucleotide; and (c) comparing the copy number by determining the amount of specific hybridization of the first and second collections of labeled nucleic acid sequences to the target elements.

2. The method of claim 1, wherein the target nucleic acid sequences are DNA.

3. The method of claim 1, wherein the first and second labeled nucleic acid sequences comprise human DNA.

4. The method of claim 3, wherein the DNA is prepared from cDNA.

5. The method of claim 1, wherein the target oligonucleotides are from about 10 to about 100 nucleotides in length.

6. The method of claim 1, wherein the solid support is glass.

7. The method of claim 1, wherein the first and second labels are fluorescent labels.

8. The method of claim 1, wherein the PCR is carried out using labeled primers.

9. The method of claim 1, wherein the first labeled nucleic acid sequences are prepared from MRNA from a test cell and the second labeled nucleic acid sequences are prepared from MRNA from a reference cell.

10. The method of claim 1, wherein the first labeled nucleic acid sequences are prepared from test genomic DNA and the second labeled nucleic acid sequences are prepared from normal reference genomic DNA.

11. The method of claim 10, wherein the test genome comprises nucleic acids from fetal tissue.

12. The method of claim 10, wherein the test genome comprises nucleic acids from a tumor.

* * * * *

UNITED STATES PATENT AND TRADEMARK OFFICE
CERTIFICATE OF CORRECTION

PATENT NO.    : 6,465,182 B1                                        Page 1 of 1
DATED         : October 15, 2002
INVENTOR(S)   : Joe Gray et al.

It is certified that error appears in the above-identified patent and that said Letters Patent is hereby corrected as shown below:

Column 1,
Line 9, delete "C58207" and insert -- CA58207 --.

Signed and Sealed this

Eleventh Day of March, 2003

JAMES E. ROGAN
*Director of the United States Patent and Trademark Office*